United States Patent
Matheny (10) Patent No.: US 9,533,072 B2
(45) Date of Patent: Jan. 3, 2017

(54) REINFORCED VASCULAR PROSTHESES

(71) Applicant: CorMatrix Cardiovascular, Inc., Roswell, GA (US)

(72) Inventor: Robert G Matheny, Norcross, GA (US)

(73) Assignee: CORMATRIX CARDIOVASCULAR, INC., Roswell, GA (US)

( * ) Notice: Subject to any disclaimer, the term of this patent is extended or adjusted under 35 U.S.C. 154(b) by 77 days.

(21) Appl. No.: 14/566,155

(22) Filed: Dec. 10, 2014

(65) Prior Publication Data
US 2015/0094796 A1    Apr. 2, 2015

Related U.S. Application Data

(63) Continuation-in-part of application No. 14/337,915, filed on Jul. 22, 2014, which is a continuation of
(Continued)

(51) Int. Cl.
*A61L 27/36*    (2006.01)
*A61F 2/06*    (2013.01)
(Continued)

(52) U.S. Cl.
CPC .............. *A61L 27/3633* (2013.01); *A61F 2/06* (2013.01); *A61F 2/07* (2013.01); *A61F 2/86* (2013.01); *A61L 27/18* (2013.01); *A61L 27/34* (2013.01); *A61L 27/3629* (2013.01); *A61L 27/38* (2013.01); *A61L 27/3834* (2013.01); *A61L 27/507* (2013.01); *A61L 27/54* (2013.01); *A61F 2002/072* (2013.01); *A61F 2210/0004* (2013.01); *A61F 2210/0014* (2013.01);
(Continued)

(58) Field of Classification Search
CPC .............. A61F 2/07; A61F 2/24; A61F 2/06; A61F 2/86; A61F 2002/046; A61F 2002/047; A61F 2002/048; A61F 2210/0057; A61F 2002/045; A61F 2250/0067; A61F 2210/0004; A61F 2002/072; A61F 2210/0014; A61L 27/18; A61L 2300/216; A61L 2300/252; A61L 2300/40; A61L 2300/41; A61L 2300/414; A61L 2300/416; A61L 2300/434; A61L 2300/64; A61L 2430/20; A61L 2430/22; A61L 27/34; A61L 27/36; A61L 27/3629; A61L 27/3633; A61L 27/38; A61L 27/3834; A61L 27/507; A61L 27/54
See application file for complete search history.

(56) References Cited

U.S. PATENT DOCUMENTS 6,015,432 A    1/2000   Rakos et al.
7,745,217 B2   6/2010   Patel et al.
(Continued)

OTHER PUBLICATIONS

Sundaram, et al., Small Diameter Vascular Graft Enigneered Using Human Embryonic Stem Cell-Derived Mesenchymal Cells, Tissue Engineering Part A, vol. 20, pp. 740-750 (2014).

*Primary Examiner* — Christian Sevilla
*Assistant Examiner* — Seema Mathew
(74) *Attorney, Agent, or Firm* — Francis Law Group (57) ABSTRACT

Vascular grafts for treating, reconstructing and replacing damaged or diseased cardiovascular vessels that are formed from decellularized extracellular matrix (ECM). The vascular grafts include outer or outer and inner coatings that provide structural reinforcement.

17 Claims, 2 Drawing Sheets

Related U.S. Application Data application No. 14/031,520, filed on Sep. 19, 2013, now abandoned, and a continuation-in-part of application No. 14/031,423, filed on Sep. 19, 2013.

(51) Int. Cl.
| | | |
|---|---|---|
| A61F 2/07 | (2013.01) | |
| A61L 27/18 | (2006.01) | |
| A61L 27/34 | (2006.01) | |
| A61L 27/38 | (2006.01) | |
| A61L 27/50 | (2006.01) | |
| A61L 27/54 | (2006.01) | |
| A61F 2/86 | (2013.01) | |

(52) U.S. Cl.
CPC ............ *A61F 2210/0076* (2013.01); *A61F 2220/0075* (2013.01); *A61F 2250/0067* (2013.01); *A61L 27/36* (2013.01); *A61L 2300/216* (2013.01); *A61L 2300/252* (2013.01); *A61L 2300/40* (2013.01); *A61L 2300/41* (2013.01); *A61L 2300/414* (2013.01); *A61L 2300/416* (2013.01); *A61L 2300/434* (2013.01); *A61L 2300/64* (2013.01); *A61L 2430/20* (2013.01); *A61L 2430/22* (2013.01)

(56) References Cited

U.S. PATENT DOCUMENTS

| 8,778,012 | B2 | 7/2014 | Matheny | |
|---|---|---|---|---|
| 2006/0009839 | A1 | 1/2006 | Tan | |
| 2006/0136047 | A1* | 6/2006 | Obermiller | A61F 2/06 623/1.41 |
| 2006/0147433 | A1* | 7/2006 | Hiles | A61K 35/37 424/93.7 |
| 2006/0257447 | A1 | 11/2006 | Hinds et al. | |
| 2007/0112411 | A1* | 5/2007 | Obermiller | A61F 2/07 623/1.13 |
| 2009/0171440 | A1* | 7/2009 | Carlson | A61F 2/06 623/1.15 |
| 2010/0268321 | A1 | 10/2010 | McDermott et al. | |
| 2012/0156255 | A1* | 6/2012 | Singh | A61K 9/0024 424/400 |
| 2012/0182609 | A1* | 7/2012 | Borenstein | B01L 3/502707 359/368 |
| 2013/0103079 | A1* | 4/2013 | Lau | A61L 17/08 606/229 |
| 2013/0116789 | A1* | 5/2013 | Chachques | A61L 27/26 623/14.13 |
| 2013/0325108 | A1 | 12/2013 | Imran et al. | |
| 2014/0066469 | A1* | 3/2014 | Robinson | A61K 31/4706 514/275 |
| 2014/0288642 | A1* | 9/2014 | Yoshida | A61L 27/16 623/2.17 |
| 2014/0309726 | A1 | 10/2014 | Wang | |
| 2015/0037293 | A1* | 2/2015 | Jun | A61L 27/22 424/93.7 |
| 2016/0030496 | A1* | 2/2016 | Prakash | A61L 31/10 424/423 |
| 2016/0143729 | A1* | 5/2016 | Matheny | A61F 2/203 623/9 |
| 2016/0199541 | A1* | 7/2016 | Yang | C08G 63/6852 424/486 |
| 2016/0256604 | A1* | 9/2016 | Hanna | A61L 27/18 |
| 2016/0302911 | A1* | 10/2016 | Soletti | A61L 27/18 |

\* cited by examiner

REINFORCED VASCULAR PROSTHESES

CROSS-REFERENCES TO RELATED APPLICATIONS

This application is a continuation-in-part of U.S. application Ser. No. 14/337,915, filed on Jul. 22, 2014, which is a continuation-in-part of U.S. application Ser. No. 14/031,520, filed on Sep. 19, 2013, which is a continuation-in-part of U.S. application Ser. No. 14/031,423, filed on Sep. 19, 2013, which claims the benefit of U.S. application Ser. No. 61/710,992, filed on Oct. 8, 2012.

FIELD OF THE INVENTION

The present invention relates to methods and apparatus for treating damaged or diseased cardiovascular vessels. More particularly, the present invention relates to reinforced vascular grafts or prostheses for treating and/or reconstructing damaged or diseased cardiovascular vessels.

BACKGROUND OF THE INVENTION

As is well known in the art, various vascular grafts or prostheses are often employed to treat and reconstruct damaged or diseased cardiovascular vessels.

Currently, the vascular grafts often employed to reconstruct (or replace) damaged or diseased cardiovascular vessels are autologous arteries and veins, e.g., internal mammary artery or saphenous vein; particularly, in situations where small diameter (i.e. 3-4 mm) vessels are required, such as below the knee and coronary artery bypass grafting.

Autologous arteries and veins are, however, often unavailable, due to prior harvest, or unsuitable, due to arterial disease.

When autologous arteries and veins are unavailable or unsuitable, synthetic polytatrafluoroethylene (PTFE) or Dacron® grafts are often employed to reconstruct or replace damaged or diseased cardiovascular vessels; particularly, in situations where large diameter (i.e. ≥6 mm) vessels are required.

There are, however, numerous drawbacks and disadvantages associated with synthetic grafts. A major drawback is the poor median patency exhibited by synthetic grafts, due to stenosis, thromboembolization, calcium deposition and infection. Indeed, it has been found that patency is >25% @ 3 years using synthetic and cryopreserved grafts in peripheral and coronary bypass surgeries, compared to >70% for autologous vascular grafts. See Chard, et al., *Aorta-Coronary Bypass Grafting with Polytetrafluoroehtylene Conduits: Early and Late Outcome in Eight Patients*, j Thorac Cardiovasc Surg, vol. 94, pp. 312-134 (1987).

Decellularized bovine internal jugular xenografts and human allograft vessels from cadavers have also employed to reconstruct or replace damaged or diseased cardiovascular vessels. Such grafts are, however, prone to calcification and thrombosis and, thus, have not gained significant clinical acceptance.

Vascular prostheses constructed of various biodegradable materials, such as poly (trimethylene carbonate), have also been developed to reconstruct damaged or diseased cardiovascular vessels. There are, however, several drawbacks and disadvantages associated with such prostheses.

One major disadvantage is that the biodegradable materials and, hence, prostheses formed therefrom, often break down at a faster rate than is desirable for the application. A further disadvantage is that the materials can, and in many instances will, break down into large, rigid fragments that can cause obstructions in the interior of the vessel.

More recently, vascular grafts comprising various remodelable materials, such as extracellular matrix sheets, have been developed to treat and reconstruct damaged or diseased cardiovascular vessels. Illustrative are the vascular grafts disclosed in Applicant's Co-Pending application Ser. No. 13/573,226.

Although such grafts have garnered overwhelming success and, hence, gained significant clinical acceptance, there are a few drawbacks associated with such grafts. Among the drawbacks are the construction and, hence, configuration of the noted vascular grafts.

As discussed in detail in Co-Pending application Ser. No. 13/573,226, such grafts typically comprise one or more sheets of ECM tissue, e.g., small intestine submucosa, which is secured at one edge to form a tubular structure. The secured edge or seam can, and in many instances will, disrupt blood flow through the graft. A poorly secured edge also poses a significant risk of thrombosis.

Further, in some instances, wherein the ECM graft comprises two or more sheets, i.e. a multi-sheet laminate, such as disclosed in Co-pending application Ser. No. 14/031,423, the laminate structure is prone to delamination.

Thus, readily available, versatile vascular grafts that are not prone to calcification, thrombosis and intimal hyperplasia would fill a substantial and growing clinical need.

It is therefore an object of the present invention to provide vascular grafts (including "endografts") that substantially reduce or eliminate (i) the risk of thrombosis, (ii) intimal hyperplasia after intervention in a vessel, (iii) the harsh biological responses associated with conventional polymeric and metal prostheses, and (iv) the formation of biofilm, inflammation and infection.

It is another object of the present invention to provide vascular grafts that can effectively replace or improve biological functions or promote the growth of new tissue in a subject.

It is another object of the present invention to provide vascular grafts that induce host tissue proliferation, bioremodeling and regeneration of new tissue and tissue structures with site-specific structural and functional properties.

It is another object of the present invention to provide vascular grafts that are capable of administering a pharmacological agent to host tissue and, thereby produce a desired biological and/or therapeutic effect.

SUMMARY OF THE INVENTION

The present invention is directed to vascular grafts or prostheses for treating, reconstructing or replacing damaged or diseased cardiovascular vessels.

As discussed in detail herein, in a preferred embodiment, the vascular grafts comprise coated tubular members having proximal and distal ends.

In some embodiments of the invention, the tubular members comprise a decellularized ECM material derived from a mammalian tissue source, i.e. tubular ECM members.

According to the invention, the ECM material can be derived from various mammalian tissue sources, including, without limitation, small intestine submucosa (SIS), urinary bladder submucosa (UBS), stomach submucosa (SS), mesothelial tissue, placental extracellular matrix, ornomentum extracellular matrix, and cardiac extracellular matrix.

In a preferred embodiment, the mammalian tissue source comprises an adolescent mammalian tissue source.

In some embodiments, the tubular members comprise an ECM/ECM-mimicking biomaterial composition comprising an ECM material and an ECM-mimicking biomaterial, such as poly(glycerol sebacate) (PGS).

In some embodiments of the invention, the tubular member coating comprises a polymeric composition comprising a biodegradable polymeric material, such as poly(ε-caprolactone) (PCL).

In some embodiments of the invention, the tubular member coating comprises an ECM composition comprising at least one ECM material.

In some embodiments of the invention, the tubular member coating comprises an ECM-mimicking biomaterial composition comprising at least one ECM-mimicking biomaterial.

In some embodiments of the invention, the tubular members further comprise an outer reinforcing structure.

In some embodiments of the invention, the reinforcing structure comprises a thin member, such as a strand, that is wound about the outer surface of the tubular member.

In some embodiments of the invention, the reinforcing structure comprises a mesh or woven structure.

In some embodiments of the invention, the reinforcing structure comprises an ECM-mimicking biomaterial, such as PGS.

In some embodiments of the invention, the tubular members and, hence, vascular grafts formed therefrom, further comprise at least one additional biologically active agent or composition, i.e. an agent that induces or modulates a physiological or biological process, or cellular activity, e.g., induces proliferation, and/or growth and/or regeneration of tissue.

In some embodiments, the biologically active agent comprises a cell, such as, without limitation, a human embryonic stem cell, fetal cardiomyocyte, myofibroblast, and mesenchymal stem cell.

In some embodiments, the biologically active agent comprises a growth factor, such as, without limitation, a transforming growth factor-alpha (TGF-α), transforming growth factor-beta (TGF-β), fibroblast growth factor-2 (FGF-2), basic fibroblast growth factor (bFGF), and vascular epithelial growth factor (VEGF).

In some embodiments, the tubular members and, hence, vascular grafts formed therefrom, further comprise at least one pharmacological agent or composition (or drug), i.e. an agent or composition that is capable of producing a desired biological effect in vivo, e.g., stimulation or suppression of apoptosis, stimulation or suppression of an immune response, etc.

Suitable pharmacological agents and compositions include, without limitation, antibiotics, anti-viral agents, analgesics, anti-inflammatories, anti-neoplastics, anti-spasmodics, and anticoagulants and/or antithrombic agents.

In some embodiments of the invention, the pharmacological agent comprises a statin, i.e. a HMG-CoA reductase inhibitor, such as cerivastatin.

In some embodiments of the invention, the vascular graft and/or coating provides a single-stage agent delivery profile, i.e. comprise a single-stage agent delivery vehicle, wherein a modulated dosage of an aforementioned biologically active and/or pharmacological agent is provided.

In some embodiments of the invention, the vascular graft and/or coating provides a multi-stage agent delivery profile, i.e. comprise a multi-stage delivery vehicle, wherein a plurality of the aforementioned biologically active and/or pharmacological agents are administered via a modulated dosage.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE PREFERRED EMBODIMENT

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a, "an" and "the" include plural referents unless the content clearly dictates otherwise. Thus, for example, reference to "a pharmacological agent" includes two or more such agents and the like.

Further, ranges can be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately", it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "about" or "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

DEFINITIONS

The terms "graft" and "endograft" are used interchangeably herein, and mean and include a structure that is configured for implantation in a cardiovascular structure, e.g., a cardiovascular vessel.

The terms "extracellular matrix" and "ECM" are used interchangeably herein, and mean and include a collagen-rich substance that is found in between cells in mammalian tissue, and any material processed therefrom, e.g. decellularized ECM. According to the invention, the ECM material can be derived from various mammalian tissue sources including, without limitation, the small intestine, large intestine, stomach, lung, liver, kidney, pancreas, placenta, heart, bladder, prostate, tissue surrounding growing enamel, tissue surrounding growing bone, and any fetal tissue from any mammalian organ.

The ECM material can thus comprise, without limitation, small intestine submucosa (SIS), urinary bladder submucosa (UBS), stomach submucosa (SS), central nervous system tissue, dermal extracellular matrix, subcutaneous extracellular matrix, gastrointestinal extracellular matrix, i.e. large and small intestines, tissue surrounding growing bone, placental extracellular matrix, ornomentum extracellular matrix, epithelium of mesodermal origin, i.e. mesothelial tissue, cardiac extracellular matrix, e.g., pericardium and/or myocardium, kidney extracellular matrix, pancreas extracellular matrix, lung extracellular matrix, and combinations thereof. The ECM material can also comprise collagen from mammalian sources.

The terms "urinary bladder submucosa (UBS)", "small intestine submucosa (SIS)" and "stomach submucosa (SS)" also mean and include any UBS and/or SIS and/or SS material that includes the tunica mucosa (which includes the transitional epithelial layer and the tunica propria), submucosal layer, one or more layers of muscularis, and adventitia (a loose connective tissue layer) associated therewith.

The ECM material can also be derived from basement membrane of mammalian tissue/organs, including, without limitation, urinary basement membrane (UBM), liver basement membrane (LBM), and amnion, chorion, allograft pericardium, allograft acellular dermis, amniotic membrane, Wharton's jelly, and combinations thereof.

Additional sources of mammalian basement membrane include, without limitation, spleen, lymph nodes, salivary glands, prostate, pancreas and other secreting glands.

The ECM material can also be derived from other sources, including, without limitation, collagen from plant sources and synthesized extracellular matrices, i.e. cell cultures.

The term "angiogenesis", as used herein, means a physiologic process involving the growth of new blood vessels from pre-existing blood vessels.

The term "neovascularization", as used herein, means and includes the formation of functional vascular networks that can be perfused by blood or blood components. Neovascularization includes angiogenesis, budding angiogenesis, intussuceptive angiogenesis, sprouting angiogenesis, therapeutic angiogenesis and vasculogenesis.

The term "Artelon™", as used herein, means a poly (urethane urea) material distributed by Artimplant AB in Goteborg, Sweden.

The terms "ECM-mimicking material" and "ECM-mimicking biomaterial" are used interchangeably herein, and mean and include a biodegradable material that induces neovascularization and bioremodeling of tissue in vivo, i.e. when disposed proximate damaged biological tissue. The terms "ECM-mimicking material" and "ECM-mimicking biomaterial" thus include, without limitation, ECM-mimicking polymeric biomaterials; specifically, poly(glycerol sebacate) (PGS).

The terms "biologically active agent" and "biologically active composition" are used interchangeably herein, and mean and include agent that induces or modulates a physiological or biological process, or cellular activity, e.g., induces proliferation, and/or growth and/or regeneration of tissue.

The terms "biologically active agent" and "biologically active composition" thus mean and include, without limitation, the following growth factors: platelet derived growth factor (PDGF), epidermal growth factor (EGF), transforming growth factor alpha (TGF-alpha), transforming growth factor beta (TGF-beta), fibroblast growth factor-2 (FGF-2), basic fibroblast growth factor (bFGF), vascular epithelial growth factor (VEGF), hepatocyte growth factor (HGF), insulin-like growth factor (IGF), nerve growth factor (NGF), platlet derived growth factor (PDGF), tumor necrosis factor alpha (TNA-alpha), and placental growth factor (PLGF).

The terms "biologically active agent" and "biologically active composition" also mean and include, without limitation, human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

The terms "biologically active agent" and "biologically active composition" also mean and include, without limitation, the following biologically active agents (referred to interchangeably herein as a "protein", "peptide" and "polypeptide"): collagen (types I-V), proteoglycans, glycosaminoglycans (GAGs), glycoproteins, growth factors, cytokines, cell-surface associated proteins, cell adhesion molecules (CAM), angiogenic growth factors, endothelial ligands, matrikines, cadherins, immuoglobins, fibril collagens, non-fibrallar collagens, basement membrane collagens, multiplexins, small-leucine rich proteoglycans, decorins, biglycans, fibromodulins, keratocans, lumicans, epiphycans, heparin sulfate proteoglycans, perlecans, agrins, testicans, syndecans, glypicans, serglycins, selectins, lecticans, aggrecans, versicans, neurocans, brevicans, cytoplasmic domain-44 (CD-44), macrophage stimulating factors, amyloid precursor proteins, heparins, chondroitin sulfate B (dermatan sulfate), chondroitin sulfate A, heparin sulfates, hyaluronic acids, fibronectins, tenascins, elastins, fibrillins, laminins, nidogen/enactins, fibulin I, fibulin II, integrins, transmembrane molecules, thrombospondins, ostepontins, and angiotensin converting enzymes (ACE).

The terms "pharmacological agent", "active agent", "drug" and "active agent formulation" are used interchangeably herein, and mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "pharmacological agent", "active agent", "drug" and "active agent formulation" thus mean and include, without limitation, antibiotics, anti-arrhythmic agents, anti-viral agents, analgesics, steroidal anti-inflammatories, non-steroidal anti-inflammatories, anti-neoplastics, anti-spasmodics, modulators of cell-extracellular matrix interactions, proteins, hormones, growth factors, matrix metalloproteinases (MMPS), enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

The terms "pharmacological agent", "active agent", "drug" and "active agent formulation" thus include, without limitation, atropine, tropicamide, dexamethasone, dexamethasone phosphate, betamethasone, betamethasone phosphate, prednisolone, triamcinolone, triamcinolone acetonide, fluocinolone acetonide, anecortave acetate, budesonide, cyclosporine, FK-506, rapamycin, ruboxistaurin, midostaurin, flurbiprofen, suprofen, ketoprofen, diclofenac, ketorolac, nepafenac, lidocaine, neomycin, polymyxin b, bacitracin, gramicidin, gentamicin, oyxtetracline, ciprofloxacin, ofloxacin, tobramycin, amikacin, vancomycin, cefazolin, ticarcillin, chloramphenicol, miconazole, itraconazole, trifluridine, vidarabine, ganciclovir, acyclovir, cidofovir, ara-amp, foscarnet, idoxuridine, adefovir dipivoxil, methotrexate, carboplatin, phenylephrine, epinephrine, dipivefrin, timolol, 6-hydroxydopamine, betaxolol, pilocarpine, carbachol, physostigmine, demecarium, dorzolamide, brinzolamide, latanoprost, sodium hyaluronate, insulin, verteporfin, pegaptanib, ranibizumab, and other antibodies, antineoplastics, anti-VEGFs, ciliary neurotrophic factor, brain-derived neurotrophic factor, bFGF, Caspase-1 inhibitors, Caspase-3 inhibitors, α-Adrenoceptors agonists, NMDA antagonists, Glial cell line-derived neurotrophic factors (GDNF), pigment epithelium-derived factor (PEDF), and NT-3, NT-4, NGF, IGF-2.

The terms "pharmacological agent", "active agent", "drug" and "active agent formulation" further mean and include the following Class I-Class V antiarrhythmic agents: (Class Ia) quinidine, procainamide and disopyramide; (Class Ib) lidocaine, phenytoin and mexiletine; (Class Ie) flecainide, propafenone and moricizine; (Class II) propranolol, esmolol, timolol, metoprolol and atenolol; (Class III) amiodarone, sotalol, ibutilide and dofetilide; (Class IV) verapamil and diltiazem) and (Class V) adenosine and digoxin.

The terms "pharmacological agent", "active agent", "drug" and "active agent formulation" further mean and include, without limitation, the following antiobiotics: aminoglycosides, cephalosporins, chloramphenicol, clindamycin, erythromycins, fluoroquinolones, macrolides, azolides, metronidazole, penicillins, tetracyclines, trimethoprim-sulfamethoxazole and vancomycin.

The terms "pharmacological agent", "active agent", "drug" and "active agent formulation" further include, without limitation, the following steroids: andranes (e.g., testosterone), cholestanes, cholic acids, corticosteroids (e.g., dexamethasone), estraenes (e.g., estradiol) and pregnanes (e.g., progesterone).

The terms "pharmacological agent", "active agent", "drug" and "active agent formulation" can further include one or more classes of narcotic analgesics, including, without limitation, morphine, codeine, heroin, hydromorphone, levorphanol, meperidine, methadone, oxycodone, propoxyphene, fentanyl, methadone, naloxone, buprenorphine, butorphanol, nalbuphine and pentazocine.

The terms "pharmacological agent", "active agent", "drug" and "active agent formulation" can further include one or more classes of topical or local anesthetics, including, without limitation, esters, such as benzocaine, chloroprocaine, cocaine, cyclomethycaine, dimethocaine/larocaine, piperocaine, propoxycaine, procaine/novacaine, proparacaine, and tetracaine/amethocaine. Local anesthetics can also include, without limitation, amides, such as articaine, bupivacaine, cinchocaine/dibucaine, etidocaine, levobupivacaine, lidocaine/lignocaine, mepivacaine, prilocaine, ropivacaine, and trimecaine. Local anesthetics can further include combinations of the above from either amides or esters.

The terms "anti-inflammatory" and "anti-inflammatory agent" are also used interchangeably herein, and mean and include a "pharmacological agent" and/or "active agent formulation", which, when a therapeutically effective amount is administered to a subject, prevents or treats bodily tissue inflammation i.e. the protective tissue response to injury or destruction of tissues, which serves to destroy, dilute, or wall off both the injurious agent and the injured tissues.

Anti-inflammatory agents thus include, without limitation, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, ciclofenac, ciclofrofen, cintazone, cliprofen, clobetasol propionate, clobetasone butyrate, clopirac, cloticasone propionate, cormethasone acetate, cortodoxone, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterolone, methandrostenolone, methenolone, methenolone acetate, methylprednisolone suleptanate, momiflumate, nabumetone, nandrolone, naproxen, naproxen sodium, naproxol, nimazone, olsalazine sodium, orgotein, orpanoxin, oxandrolane, oxaprozin, oxyphenbutazone, oxymetholone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, triflumidate, zidometacin, and zomepirac sodium.

The term "pharmacological composition", as used herein, means and includes a composition comprising a "pharmacological agent" and/or a "biologically active agent" and/or any additional agent or component identified herein.

The term "therapeutically effective", as used herein, means that the amount of the "pharmacological agent" and/or "biologically active agent" and/or "pharmacological composition" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The term "adolescent", as used herein, means and includes a mammal that is preferably less than three (3) years of age.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term "comprise" and variations of the term, such as "comprising" and "comprises," means "including, but not limited to" and is not intended to exclude, for example, other additives, components, integers or steps.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

As stated above, the present invention is directed to vascular grafts or prostheses for treating, reconstructing or replacing damaged or diseased tissue.

It is, however, understood that, although the disclosure is directed to vascular grafts, the invention is also applicable to coated planar members.

In a preferred embodiment, the vascular grafts comprise coated tubular members having proximal and distal ends.

In some embodiments of the invention, the tubular members comprise an ECM material derived from a mammalian tissue source. According to the invention, the mammalian tissue sources can include, without limitation, the small intestine, large intestine, stomach, lung, liver, kidney, pancreas, placenta, heart, bladder, prostate, tissue surrounding growing enamel, tissue surrounding growing bone, and any fetal tissue from any mammalian organ.

As discussed in detail herein, in a preferred embodiment, the ECM material comprises ECM selected from the group comprising, without limitation, SIS, UBS, SS, central nervous system tissue, dermal extracellular matrix, subcutaneous extracellular matrix, gastrointestinal extracellular matrix, tissue surrounding growing bone, placental extracellular matrix, omomentum extracellular matrix, mesothelial tissue, cardiac extracellular matrix, kidney extracellular matrix, pancreas extracellular matrix, lung extracellular matrix, and combinations thereof.

Preferably, the mammalian tissue source comprises an adolescent mammalian tissue source, i.e. an adolescent mammal, such as a piglet, which is preferably less than three (3) years of age.

In a preferred embodiment, the ECM material is decellularized and, hence, remodelable.

According to the invention, the ECM material can be decellularized by various conventional means. In a preferred embodiment, the ECM material is decellularized via one of the unique Novasterilis processes disclosed in U.S. Pat. No. 7,108,832 and U.S. patent applicaiton Ser. No. 13/480,204; which are incorporated by reference herein in their entirety.

In some embodiments of the invention, the tubular members comprise an ECM/ECM-mimicking biomaterial composition comprising an ECM material and an ECM-mimicking biomaterial.

In a preferred embodiment, the ECM-mimicking biomaterial comprises poly(glycerol sebacate) (PGS).

As discussed in detail below, Applicant has found that PGS exhibits numerous beneficial properties that provide several beneficial biochemical actions or activities.

PGS Physical Properties

PGS is a condensate of the non-immunogenic compositions glycerol (a simple sugar alcohol) and sebacic acid (a naturally occurring dicarboxylic acid), wherein, glycerol and sebacic acid are readily metabolized when proximate mammalian tissue. The non-immunogenic properties substantially limit the acute inflammatory responses typically associated with other "biocompatible" polymers, such as ePTFE (polytetrafluoroethylene), that are detrimental to bioremodeling and tissue regeneration.

The mechanical properties of PGS are substantially similar to that of biological tissue. Indeed, the value of the Young's modulus of PGS is between that of a ligament (in KPa range) and tendon (in GPa range). The strain to failure of PGS is also similar to that of arteries and veins (i.e. over 260% elongation).

The tensile strength of the PGS is at least $0.28 \pm 0.004$ MPa. The Young's modulus and elongation are at least $0.122 \pm 0.0003$ and at least $237.8 \pm 0.64\%$, respectively. For applications requiring stronger mechanical properties and a slower biodegradation rate, PGS can be blended with PCL, i.e. a biodegradable elastomer.

ECM Mimicking Properties/Actions

It has been established that PGS induces tissue remodeling and regeneration when administered proximate to damaged tissue, thus, mimicking the seminal regenerative properties of ECM and, hence, an ECM composition formed therefrom. The mechanism underlying this behavior is deemed to be based on the mechanical and biodegradation kinetics of the PGS. See Sant, et al., *Effect of Biodegradation and de novo Matrix Synthesis on the Mechanical Properties of VIC-seeded PGS-PCL scaffolds*, Acta. Biomater., vol. 9(4), pp. 5963-73 (2013).

In some embodiments, the ECM/ECM-mimicking biomaterial composition further comprises PCL, which, according to the invention, modulates the degradation characteristics of the composition and, hence, tubular member formed therewith.

In some embodiments, the ECM/ECM-mimicking biomaterial tubular members are formed via a Novasterilis process disclosed in U.S. Pat. No. 7,108,832 and U.S. patent application Ser. No. 13/480,204, wherein the PGS (and PCL, if employed) is driven into an ECM tubular member.

In some embodiments, the tubular members comprise a mesh structure, such as disclosed in U.S. patent application Ser. Nos. 14/554,730, 14/554,795 and 14/554,847, filed on Nov. 26, 2014.

In some embodiments, the mesh structure is embedded in the tubular member.

In some embodiments, the mesh structure is disposed over the luminal surface of the tubular member.

In some embodiments of the invention, the tubular member coating comprises a polymeric composition comprising at least one biocompatible polymeric material.

According to the invention, the biocompatible polymeric material can comprise, without limitation, polyglycolide (PGA), polylactide (PLA), poly(ϵ-caprolactone) (PCL), poly dioxanone (a polyether-ester), poly lactide-co-glycolide, polyamide esters, polyalkalene esters, polyvinyl esters, polyvinyl alcohol, and polyanhydrides, and like polymers.

The biocompatible polymeric material can also comprise, without limitation, natural polymeric materials, including, without limitation, polysaccharides (e.g. starch and cellulose), proteins (e.g., gelatin, casein, silk, wool, etc.), and polyesters (e.g., polyhydroxyalkanoates).

In some embodiments of the invention, the coating comprises a polymeric composition comprising a biocompatible polymeric material selected from the group comprising, without limitation, polyhydroxyalkonates (PHAs), polylactides (PLLA) and polyglycolides (PLGA) and their copolymers, for example poly(ϵ-caprolactone-co-glycolide), polyanhydrides, and like polymers.

According to the invention, the polymeric material can also comprise a hydrogel, including, without limitation, polyurethane, poly(ethylene glycol), poly(propylene glycol), poly(vinylpyrrolidone), xanthan, methyl cellulose, carboxymethyl cellulose, alginate, hyaluronan, poly(acrylic acid), polyvinyl alcohol, acrylic acid, hydroxypropyl methyl cellulose, methacrylic acid, $\alpha\beta$-glycerophosphate, $\kappa$-carrageenan, 2-acrylamido-2-methylpropanesulfonic acid, and $\beta$-hairpin peptide.

In some embodiments, the hydrogel is crosslinked via chemically and/or photocuring, e.g. ultraviolet light.

In some embodiments, the polymeric material is plasma treated to accommodate hygroscopic agents.

In some embodiments of the invention, the tubular member coating comprises an ECM composition comprising at least one of the aforementioned ECM materials.

Suitable ECM compositions are disclosed in U.S. Pat. Nos. 8,568,761, 8,753,885, 8,795,728, 8,734,841, 8,642,084, 8,771,737, 8,734,842, 8,784,891, 8,753,886, 8,785,197, 8,785,198, 8,735,155 and U.S. patent application Ser. No. 13/732,943, filed on Jan. 2, 2013, Ser. No. 11/448,351, filed on Jun. 6, 2006, Ser. No. 14/269,324, filed on May 5, 2014, Ser. No. 13/732,558, filed on Jan. 2, 2013, Ser. No. 13/732,731, filed on Jan. 2, 2013, Ser. No. 13/875,017, filed on May 1, 2013, Ser. No. 13/875,043, filed on May 1, 2013, Ser. No. 13/875,058, filed on May 1, 2013, Ser. No. 14/452,707, filed on Aug. 6, 2014, Ser. No. 14/192,973, filed on Jan. 28, 2014, Ser. No. 14/192,992, filed on Feb. 28, 2014, Ser. No. 14/193,008, filed on Feb. 28, 2014, Ser. No. 14/193,030, filed on Feb. 28, 2014, Ser. No. 14/193,053, filed on Feb. 28, 2014, Ser. No. 14/269,414, filed on Mar. 3, 2013, Ser. No. 14/269,487, filed on Mar. 3, 2013, Ser. No. 14/269,874, filed on Mar. 3, 2013, Ser. No. 14/337,460, filed on Mar. 3, 2013; which are incorporated by reference herein in their entirety.

In some embodiments of the invention, the tubular member coating comprises an ECM-mimicking composition comprising at least one ECM-mimicking biomaterial.

In a preferred embodiment, the ECM-mimicking biomaterial comprises PGS.

In some embodiments of the invention, the tubular member coating comprises an ECM-mimicking composition comprising PGS and PCL.

In some embodiments of the invention, the tubular member coating comprises an ECM/ECM-mimicking biomaterial composition, e.g. 50% ECM/50% PGS.

In some embodiments, the ECM/ECM-mimicking biomaterial composition further comprises PCL.

In some embodiments, the tubular member coating comprises a blended plurality of ECM, polymeric, ECM-mimicking biomaterial composition, and/or ECM/ECM-mimicking biomaterial composition coatings.

In some embodiments, the tubular member coating comprises a porosity in the range of 10-90%.

In some embodiments, the tubular member coating comprises a thickness in the range of 5-100 µm, which can vary based on the orientation and the size of the vascular grafts. In some embodiments, the coating thickness is in the range of 10-20 µm. If multiple coatings are employed, the total coating thickness is preferably in the range of 5-200 µm, more preferably, in the range of 30-80 µm.

According to the invention, the tubular member coating(s) can be applied to the tubular member by various conventional means, including, without limitation, pressure coating in a vapor chamber, dip coating, and spraying.

In some embodiments of the invention, the tubular members further comprise an outer reinforcing structure, such as disclosed in Co-pending U.S. application Ser. No. 14/337,863, filed on Jul. 22, 2014, and Ser. Nos. 14/554,730, 14/554,795 and 14/554,847, filed on Nov. 26, 2014, which are incorporated by reference herein in their entirety.

According to the invention, the reinforcing structure can comprise a wound member or strand configuration, i.e. a thin strand wound around the outer surface of the tubular member, such as disclosed in Co-Pending application Ser. No. 14/337,863 or a mesh structure, such as disclosed in Co-Pending application Ser. Nos. 14/554,730, 14/554,795 and 14/554,847.

In some embodiments of the invention, the reinforcing structure comprises one of the aforementioned ECM materials.

In some embodiments, the reinforcing structure comprises one of the aforementioned polymeric materials.

In some embodiments of the invention, the reinforcing structure comprises one of the aforementioned ECM-mimicking biomaterial compositions.

In some embodiments of the invention, the reinforcing structure comprises one of the aforementioned ECM/ECM-mimicking biomaterial compositions.

In some embodiments of the invention, the reinforcing structure comprises a biocompatible metal, such as stainless steel and Nitinol®.

As stated above, in some embodiments of the invention, the tubular members of the invention and, hence, vascular grafts formed therefrom and tubular member coatings further comprise at least one additional biologically active agent or composition, i.e. an agent that induces or modulates a physiological or biological process, or cellular activity, e.g., induces proliferation, and/or growth and/or regeneration of tissue.

In a preferred embodiment, the biologically active agent is similarly derived from an adolescent mammal, i.e. a mammal less than three (3) years of age.

Suitable biologically active agents include any of the aforementioned biologically active agents, including, without limitation, the aforementioned cells and proteins.

In some embodiments of the invention, the biologically active agent specifically comprises a growth factor selected from the group comprising transforming growth factor-alpha (TGF-α), transforming growth factor-beta (TGF-β), fibroblast growth factor-2 (FGF-2), basic fibroblast growth factor (bFGF) and vascular epithelial growth factor (VEGF).

According to the invention, upon implanting a tubular member and, hence, a vascular graft formed therefrom proximate damaged biological tissue of a subject, the growth factors link to and interact with at least one molecule in the tubular member and/or a cell or molecule recruited by the ECM and enhances cell and tissue proliferation, bioremodeling, and regeneration of new tissue structures.

By way of example, according to the invention, when a tubular member and, hence, a vascular graft formed therefrom comprises a growth factor augmented ECM composition and/or an ECM composition coating comprising ECM and an exogenously added growth factor, e.g. bFGF and/or VEGF, and the tubular member is disposed proximate damaged biological tissue, the growth factor interacts with the endogenous heparin sulfate present in the ECM and cells recruited by the ECM, wherein the tubular member modulates inflammation and induces tissue proliferation, neovascularization, bioremodeling and regeneration of tissue.

In some embodiments of the invention, the biologically active agent comprises a protein selected from the group comprising, without limitation, collagen (types I-V), proteoglycans, glycosaminoglycans (GAGS), glycoproteins, heparins, chondroitin sulfate B (dermatan sulfate), chondroitin sulfate A, heparin sulfates, hyaluronic acids, cytokines, cell-surface associated proteins, and cell adhesion molecules (CAMs).

In some embodiments of the invention, the cytokine is selected from the group comprising a stem cell factor (SCF), stromal cell-derived factor-1 (SDF-1), granulocyte macrophage colony-stimulating factor (GM-CSF), interferon gamma (IFN-gamma), interleukin-3, interleukin-4, interleukin-8, interleukin-10, interleukin-13, leukemia inhibitory factor (LIF), amphiregulin, thrombospondin 1, thrombospondin 2, thrombospondin 3, thrombospondin 4, thrombospondin 5, and angiotensin converting enzyme (ACE).

According to the invention, when a tubular member and, hence, a vascular graft formed therefrom comprises a protein augmented ECM composition and/or an ECM composition coating comprising ECM and an exogenously added protein, e.g., cytokine, the protein similarly interacts with at least one molecule in the tubular member and/or a cell or molecule recruited by the ECM and similarly enhances cell and tissue proliferation, bioremodeling, and regeneration of new tissue structures.

In some embodiments, the tubular members of the invention and, hence, vascular grafts formed therefrom and tubular member coatings further comprise at least one pharmacological agent or composition (or drug), i.e. an agent or composition that is capable of producing a desired biological effect in vivo, e.g., stimulation or suppression of apoptosis, stimulation or suppression of an immune response, etc.

Suitable pharmacological agents and compositions include any of the aforementioned agents, including, without limitation, antibiotics, anti-viral agents, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

In some embodiments of the invention, the pharmacological agent comprises one of the aforementioned anti-inflammatory agents.

In some embodiments of the invention, the pharmacological agent comprises a statin, i.e. a HMG-CoA reductase inhibitor. According to the invention, suitable statins include, without limitation, atorvastatin (Lipitor®), cerivastatin, fluvastatin (Lescol®), lovastatin (Mevacor®, Altocor®, Altoprev®), mevastatin, pitavastatin (Livalo®, Pitava®), pravastatin (Pravachol®, Selektine®, Lipostat®), rosuvastatin (Crestor®), and simvastatin (Zocor®, Lipex®). Several actives comprising a combination of a statin and another agent, such as ezetimbe/simvastatin (Vytorin®), are also suitable.

Applicant has found that the noted statins exhibit numerous beneficial properties that provide several beneficial biochemical actions or activities; particularly, when delivered to damaged tissue with an ECM material. Indeed, Applicant has found that when a statin is added to ECM (wherein a statin augmented ECM composition is formed) and the statin augmented ECM composition is administered to damaged tissue, the statin interacts with the cells recruited by the ECM, wherein the statin augmented ECM composition modulates inflammation of the damaged tissue by modulating several significant inflammatory processes, including restricting expression of monocytes chemoattractant protein 1 (MCP-1) and chemokine (C—C) motif ligand 2 (CCR2).

The properties and beneficial actions are further discussed in Applicant's Co-Pending application Ser. No. 13/328,287, filed on Dec. 16, 2011, Ser. No. 13/373,569, filed on Sep. 24, 2012 and Ser. No. 13/782,024, filed on Mar. 1, 2013; which are incorporated by reference herein in their entirety.

Additional suitable pharmacological agents and compositions that can be employed within the scope of the invention are disclosed in Pat. Pub. Nos. 20070014874, 20070014873, 20070014872, 20070014871, 20070014870, 20070014869, and 20070014868; which are expressly incorporated by reference herein in its entirety.

According to the invention, the biologically active and pharmacological agents referenced above can comprise various forms.

In some embodiments of the invention, the biologically active and pharmacological agents, e.g. simvastatin, comprise microcapsules that provide delayed delivery of the agent contained therein.

In some embodiments, the tubular members of the invention and, hence, vascular grafts formed therefrom comprise a combination of ECM, polymeric, ECM-mimicking biomaterial composition, and/or ECM/ECM-mimicking biomaterial composition coatings having various biologically active and/or pharmacological agents and/or properties, e.g. a an ECM composition coating comprising a growth factor and an ECM-mimicking biomaterial composition coating comprising a pharmacological agent, e.g. antiinflammatory.

In some embodiments, the tubular member coatings comprise modulated degradation kinetics, wherein the gradual degradation of the coating provides a controlled release of biologically active and/or pharmacological agents incorporated therein.

In some embodiments, the tubular member coatings are configured to provide a delivery gradient of various biologically active and/or pharmacological agent delivery profiles. By way of example, in some embodiments, biologically active and/or pharmacological agents are disposed throughout various depths or thickness ranges of one or more coatings.

In some embodiments, the tubular members of the invention and, hence, vascular grafts formed therefrom specifically comprise an ECM composition coating comprising anti-inflammatory growth factors interleukin-10 (IL-10) and transforming growth factor beta (TGF-β), which will suppress the inflammatory reaction leading to a chronic immune response. According to the invention, during a chronic immune response, IL-10 and TGF-β induce the expression of tissue inhibitor of metalloproteinase (TIMP), which inhibits matrix metalloproteinases (MMPs) that are responsible for ECM degradation during the inflammatory response. Additionally, IL-10 and TGF-β promote the recruitment of fibroblasts, which are the seminal cells responsible for ECM deposition and bioremodeling. As a result, IL-10, TGF-β, and the TIMPs concomitantly promote ECM deposition and preservation, which thus augments "modulated healing," as defined herein.

In some embodiments, the tubular members of the invention and, hence, vascular grafts formed therefrom specifically comprise an ECM composition coating comprising at least one biologically active or pharmacological agent that provides a reinforcing anti-inflammatory effect either through direct reinforcement, i.e. targeting the same inflammatory signaling pathway, or indirect reinforcement, i.e. targeting an alternate inflammatory signaling pathway. An example of direct reinforcement includes, without limitation, a combination of IL-10, TGF-β and a glucocorticoid, all of which inhibit the expression of seminal inflammatory cytokine interleukin-1 (IL-1). An example of indirect reinforcement includes, without limitation, a combination of IL-10, TGF-β and an NSAID, (Non-steroidal anti-inflammatory drug) where IL-10 and TGF-β inhibit IL-1, and the NSAIDs inhibit the activity of both cyclooxygenase-1 (COX-1) and cyclooxygenase-2 (COX-2), and thereby, the synthesis of prostaglandins and thromboxanes.

According to the invention and indicated above, upon implanting a tubular member of the invention and, hence, a vascular graft formed therefrom to damaged or diseased biological tissue, "modulated healing" is effectuated. The tubular member also provides a vessel having a smooth, non-thrombogenic interior surface.

The term "modulated healing", as used herein, and variants of this language generally refer to the modulation (e.g., alteration, delay, retardation, reduction, etc.) of a process involving different cascades or sequences of naturally occurring tissue repair in response to localized tissue damage or injury, substantially reducing their inflammatory effect. Modulated healing, as used herein, includes many different biologic processes, including epithelial growth, fibrin deposition, platelet activation and attachment, inhibition, proliferation and/or differentiation, connective fibrous tissue production and function, angiogenesis, and several stages of acute and/or chronic inflammation, and their interplay with each other.

For example, in some embodiments, the tubular members of the invention and, hence, vascular grafts formed therefrom are specifically formulated (or designed) to alter, delay, retard, reduce, and/or detain one or more of the phases associated with healing of damaged tissue, including, but not limited to, the inflammatory phase (e.g., platelet or fibrin deposition), and the proliferative phase when in contact with biological tissue.

In some embodiments, "modulated healing" refers to the ability of a tubular member of the invention and, hence, a vascular graft formed therefrom to restrict the expression of inflammatory components. By way of example, as indicated above, when a tubular member comprises an ECM or ECM/ECM-mimicking biomaterial composition and/or an ECM or ECM/ECM-mimicking biomaterial composition coating comprising a statin and the tubular member is disposed proximate damaged biological tissue, the tubular member restricts the expression of MCP-1 and CCR2.

In some embodiments, "modulated healing" means and includes the ability of a tubular member of the invention and, hence, a vascular graft formed therefrom to alter a substantial inflammatory phase (e.g., platelet or fibrin deposition) at the beginning of the tissue healing process. As used herein, the phrases "alter a substantial inflammatory phase" refers to the ability of a tubular member to substantially reduce the inflammatory response at an injury site when in contact with biological tissue.

In such an instance, a minor amount of inflammation may ensue in response to tissue injury, but this level of inflammation response, e.g., platelet and/or fibrin deposition, is substantially reduced when compared to inflammation that takes place in the absence of a tubular member and, hence, graft of the invention.

The term, "modulated healing" also refers to the ability of a tubular member of the invention and, hence, a vascular graft formed therefrom to induce host tissue proliferation, bioremodeling, including neovascularization, e.g., vasculogenesis, angiogenesis, and intussusception, and regeneration of tissue structures with site-specific structural and functional properties.

Thus, in some embodiments, the term "modulated healing" also refers to the ability of a tubular member and, hence, a vascular graft formed therefrom to modulate inflammation and/or induce host tissue proliferation and remodeling. Again, by way of example, according to the invention, when a tubular member comprises an ECM or ECM/ECM-mimicking biomaterial composition and/or an ECM or ECM/ECM-mimicking biomaterial composition coating comprising a statin and the tubular member is disposed proximate damaged biological tissue, the statin interacts with the cells recruited by the ECM, wherein the tubular modulates inflammation by, among other actions, restricting expression of MCP-1 and CCR2 and induces tissue proliferation, bioremodeling and regeneration of tissue structures with site specific structural and functional properties.

By way of a further example, according to the invention, when a tubular member and, hence, a vascular graft formed therefrom comprises a growth factor augmented ECM composition and/or a coating comprising an ECM composition comprising ECM and an exogenously added growth factor, e.g. TGF-β, is disposed proximate damaged biological tissue, the growth factor similarly interacts with the ECM and cells recruited by the ECM, wherein the tubular member modulates inflammation and induces tissue proliferation, bioremodeling and regeneration of tissue.

In some embodiments, the tubular members of the invention and, hence, vascular grafts formed therefrom and/or tubular member coatings provide a single-stage agent delivery profile, i.e. comprise a single-stage delivery vehicle, wherein a modulated dosage of an aforementioned biologically active and/or pharmacological agent is provided.

According to the invention, the term "modulated dosage" as used herein, and variants of this language generally refer to the modulation (e.g., alteration, delay, retardation, reduction, etc.) of a process involving different eluting or dispersal rates of an agent within biological tissue.

In some embodiments, the single-stage delivery vehicle comprises encapsulated particulates of a biologically active and/or pharmacological agent.

In some embodiments, the encapsulation composition comprises one of the aforementioned ECM compositions.

In some embodiments, the encapsulation composition comprises a biodegradable polymeric composition comprising one of the aforementioned polymeric materials.

In some embodiments, the encapsulation composition comprises one of the aforementioned ECM-mimicking biomaterial compositions.

In some embodiments, the encapsulation composition comprises one of the aforementioned ECM/ECM-mimicking biomaterial compositions.

In some embodiments, the encapsulation composition comprises an osmotic fluctuation inducing composition. According to the invention, suitable osmotic fluctuation inducing compositions include, without limitation, polyethylene glycol, alginate and dextran.

According to the invention, the term "osmotic fluctuation" as used herein, and variants of this language generally refer to the modulation of the osmotic pressure gradient across a defined barrier.

For example, as is well known in the art, alginate is capable of absorbing 200-300 times its weight in water, which substantially increases the osmotic pressure gradient of the alginate. The increased osmotic pressure gradient of the alginate results in a rapid dispersal of an agent therefrom.

In some embodiments of the invention, the tubular members of the invention and, hence, vascular grafts formed therefrom and/or tubular member coatings provide a multi-stage agent delivery profile, i.e. comprise a multi-stage agent delivery vehicle, wherein a plurality of the aforementioned biologically active and/or pharmacological agents are administered via a modulated dosage. By way of example, in some embodiments, the multi-stage delivery vehicle comprises encapsulated particulates comprising an antibiotic composition encapsulated in an alginate composition having a statin incorporated therein, which provides a tiered modulated agent delivery.

In some embodiments, the multi-stage agent delivery vehicle comprises a combination of different biologically active and/or pharmacological agents. By way of example, in some embodiments, the multi-stage delivery vehicle comprises encapsulated particulates comprising an encapsulated growth factor concomitantly administered with an encapsulated anti-inflammatory.

In some embodiments, the multi-stage delivery vehicle comprises a plurality of different biologically active and/or pharmacological agents encapsulated in different encapsulation compositions. By way of example, in some embodiments, the multi-stage delivery vehicle comprises encapsulated particulates comprising a growth factor encapsulated in alginate composition and a pharmacological agent encapsulated in a PGS composition.

In some embodiments of the invention, the vascular grafts further comprise at least one anchoring mechanism, such as disclosed in Co-pending application Ser. Nos. 13/782,024 and 13/686,131; which are incorporated by reference herein in their entirety.

Figure 1A:
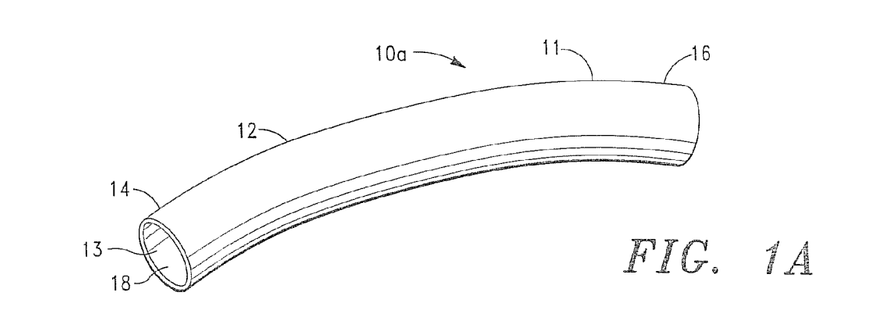
FIG. 1A is a perspective view of one embodiment of a tubular ECM member, in accordance with the invention.
Figure 1B:
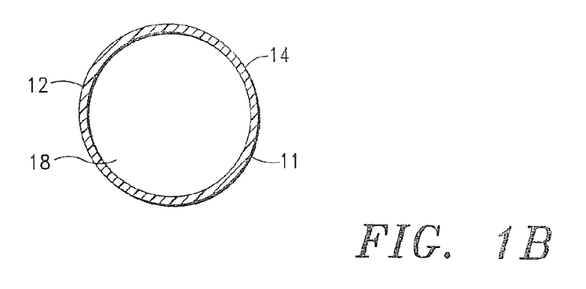
FIG. 1B is a side or edge plan view of the tubular ECM member shown in FIG. 1A, in accordance with the invention.

Referring now to FIGS. 1A and 1B, there is shown one embodiment of a tubular member of the invention. As illustrated in FIG. 1A, the tubular member 12 comprises a continuous member having proximal 14 and distal 16 ends, and a lumen 18 that extends therethrough.

As indicated above, in a preferred embodiment of the invention, the tubular member 12 comprises a decellularized ECM material. As also indicated above, preferably, the ECM material is derived from an adolescent mammal, i.e. a mammal less than three (3) years of age.

According to the invention, the tubular member 12, and, hence vascular grafts 10a and 10b (discussed below) formed therefrom, can have various diameters, e.g. 3.0 mm, 10.0 mm, etc.

In some embodiments of the invention, the tubular member 12 (or ECM material thereof) further comprises at least one additional biologically active agent or composition, i.e. an agent that induces or modulates a physiological or biological process, or cellular activity, e.g., induces proliferation, and/or growth and/or regeneration of tissue.

Suitable biologically active agents include any of the aforementioned biologically active agents, including, without limitation, the aforementioned cells, growth factors and proteins.

In some embodiments, the tubular member 12 (or ECM material thereof) further comprises at least one pharmacological agent or composition (or drug), i.e. an agent or composition that is capable of producing a desired biological effect in vivo, e.g., stimulation or suppression of apoptosis, stimulation or suppression of an immune response, etc.

Suitable pharmacological agents and compositions include any of the aforementioned agents, including, without limitation, antibiotics, anti-viral agents, analgesics, and anti-inflammatories.

In some embodiments of the invention, the pharmacological agent comprises a statin, i.e. a HMG-CoA reductase inhibitor.

Figure 2A:
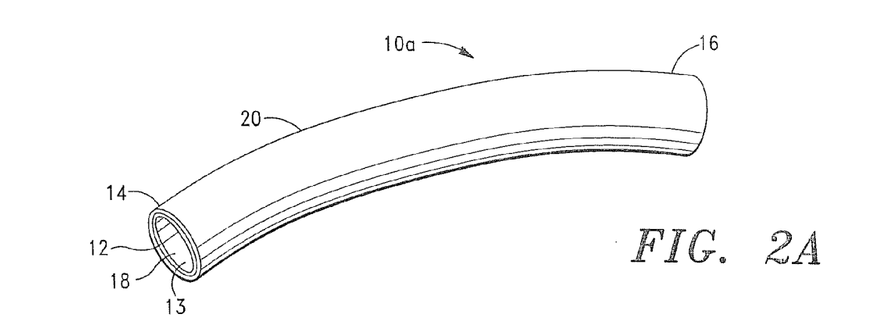
FIG. 2A is a perspective view of one embodiment of a coated ECM vascular graft, in accordance with the invention.
Figure 2B:
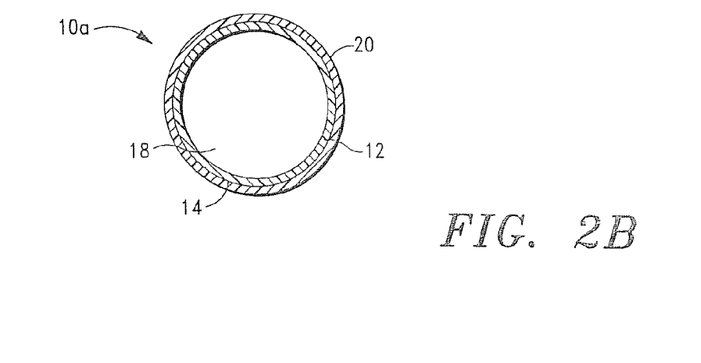
FIG. 2B is a side or edge plan view of the coated ECM vascular graft shown in FIG. 2A, in accordance with the invention.

Referring now to FIGS. 2A and 2B, there is shown one embodiment of a vascular graft of the invention. As illustrated in FIG. 2A, the graft 10a comprises tubular member 12 having proximal 14 and distal 16 ends, and a lumen 18 that extends therethrough. The tubular member 12 further comprises at least one outer coating 20 disposed on the outer surface 11 of the tubular member 12.

According to the invention, the coating 20 can comprise any of the aforementioned coatings and/or a combination thereof.

Figure 3A:
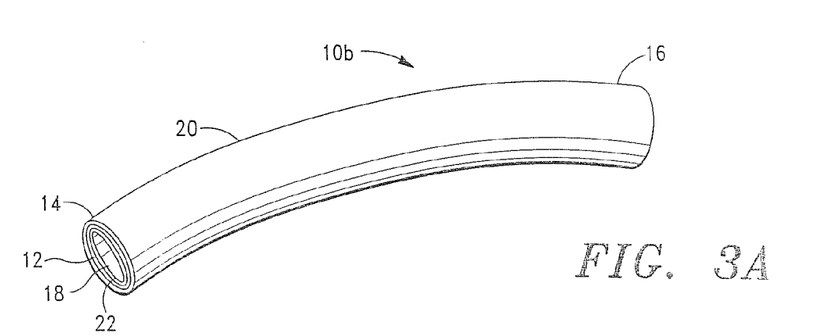
FIG. 3A is a perspective view of another embodiment of a coated ECM vascular graft, in accordance with the invention.
Figure 3B:
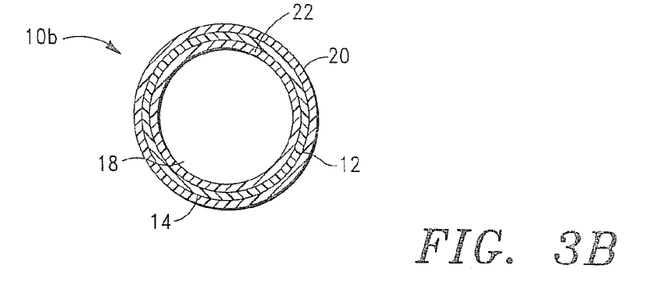
FIG. 3B is a side or edge plan view of the coated ECM vascular graft shown in FIG. 3A, in accordance with the invention.

Referring now to FIGS. 3A and 3B, there is shown another embodiment of a vascular graft of the invention. As illustrated in FIG. 3A, the graft 10b similarly comprises tubular member 12 having at least one inner coating outer coating 20 disposed on the outer surface 11 of the tubular member 12. In this embodiment, the tubular member 12 further comprises at least one inner coating 22 disposed on the inner surface 13 (or lumen surface) of the tubular member 12.

According to the invention, the inner coating 22 can similarly comprise any of the aforementioned coatings and/or or a combination thereof.

As will readily be appreciated by one having ordinary skill in the art, the present invention provides numerous advantages compared to prior art prosthetic valves. Among the advantages are the following:

The provision of vascular grafts that substantially reduce or eliminate (i) the risk of thrombosis, (ii) intimal hyperplasia after intervention in a vessel, (iii) the harsh biological responses associated with conventional polymeric and metal prostheses, and (iv) the formation of biofilm, inflammation and infection.

The provision of vascular grafts, which can be effectively employed to treat, reconstruct, replace and improve biological functions or promote the growth of new cardiovascular tissue in a cardiovascular structure.

The provision of vascular grafts that induce host tissue proliferation, bioremodeling and regeneration of new tissue and tissue structures with site-specific structural and functional properties.

The provision of vascular grafts, which are capable of administering a pharmacological agent to host tissue and, thereby produce a desired biological and/or therapeutic effect.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A vascular graft for treating damaged or diseased tissue in cardiovascular vessels, comprising:

a biodegradable and remodelable tubular member comprising an extracellular matrix (ECM) composition comprising acellular ECM from a mammalian tissue source and a growth factor selected from the group consisting of a transforming growth factor-alpha (TGF-α), transforming growth factor-beta (TGF-β), fibroblast growth factor-2 (FGF-2), and vascular epithelial growth factor (VEGF), said tubular member comprising an outer surface and a lumen that extends therethrough, said lumen defining a tubular member inner surface;

said tubular member further comprising at least one biodegradable coating disposed on said tubular member outer surface, said biodegradable coating comprising an ECM-mimicking biomaterial composition comprising poly(glycerol sebacate), said tubular member further comprises a first reinforcing structure disposed proximate the outer surface, said first reinforcing structure comprises poly (glycerol sebacate), said tubular member being configured to induce modulated healing when disposed proximate damaged cardiovascular tissue, said modulated healing comprising modulation of inflammation of said damaged tissue, and induced host tissue proliferation, bioremodeling of said damaged tissue, and regeneration of new cardiovascular tissue and tissue structures with site specific structural and functional properties.

2. The vascular graft of claim 1, wherein said mammalian tissue source is selected from the group consisting of small intestine submucosa (SIS), urinary bladder submucosa (UBS), urinary basement membrane (UBM), liver basement membrane (LBM), stomach submucosa (SS), and mesothelial tissue.

3. The vascular graft of claim 2, wherein said ECM composition further comprises at least one supplemental biologically active agent.

4. The vascular graft of claim 3, wherein said supplemental biologically active agent comprises a cell selected from the group consisting of a human embryonic stem cell, fetal cardiomyocyte, myofibroblast, and mesenchymal stem cell.

5. The vascular graft of claim 1, wherein said acellular ECM material comprises adolescent acellular ECM.

6. The vascular graft of claim 1, wherein said ECM composition further comprises a pharmacological agent.

7. The vascular graft of claim 6, wherein said pharmacological agent comprises an agent selected from the group consisting of an antibiotic, anti-viral agent, analgesic, anti-inflammatory, anti-neoplastic, anti-spasmodic, anticoagulant and antithrombotic agent.

8. The vascular graft of claim 6, wherein said pharmacological agent comprises a statin selected from the group consisting of atorvastatin, cerivastatin, fluvastatin, lovastatin, mevastatin, pitavastatin, pravastatin, rosuvastatin and simvastatin.

9. The vascular graft of claim 8, wherein said statin is encapsulated in a second osmotic fluctuation inducing composition.

10. The vascular graft of claim 9, wherein said tubular member comprises a multi-stage delivery vehicle.

11. The vascular graft of claim 1, wherein said first reinforcing structure comprises a woven structure.

12. The vascular graft of claim 1, wherein said first reinforcing structure comprises a second polymeric composition coating comprising a polymeric material selected from the group consisting of poly(ε-caprolactone-co-glycolide) (PCL), polyhydroxy-alkonate (PHA), polylactide (PLLA) and polyglycolide (PLGA) and its copolymers, and polyanhydride.

13. The vascular graft of claim 1, wherein said tubular member further comprises a second reinforcing structure.

14. The vascular graft of claim 13, wherein said second reinforcing structure comprises a mesh structure.

15. The vascular graft of claim 14, wherein said mesh reinforcing structure comprises Nitinol®.

16. The vascular graft of claim 1, wherein said growth factor is encapsulated in a first osmotic fluctuation inducing composition.

17. The vascular graft of claim 1, wherein said acellular ECM comprises acellular ECM selected from the group consisting of subcutaneous extracellular matrix, large intestine extracellular matrix, placental extracellular matrix, omentum extracellular matrix, heart extracellular matrix and lung extracellular matrix.

* * * * *